(12) United States Patent
Ando et al.

(10) Patent No.: US 11,559,205 B2
(45) Date of Patent: Jan. 24, 2023

(54) BIOLOGICAL MEASURING DEVICE AND HEAD MOUNTED DISPLAY APPARATUS

(71) Applicant: Panasonic Intellectual Property Management Co., Ltd., Osaka (JP)

(72) Inventors: Takamasa Ando, Osaka (JP); Teruhiro Shiono, Osaka (JP); Masaaki Yanagida, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 448 days.

(21) Appl. No.: 16/782,090

(22) Filed: Feb. 5, 2020

(65) Prior Publication Data

US 2020/0170512 A1 Jun. 4, 2020

Related U.S. Application Data

(63) Continuation of application No. PCT/JP2018/025433, filed on Jul. 5, 2018.

(30) Foreign Application Priority Data

Aug. 24, 2017 (JP) .............................. JP2017-161282

(51) Int. Cl.
*A61B 6/00* (2006.01)
*A61B 5/00* (2006.01)
(Continued)

(52) U.S. Cl.
CPC ............ *A61B 5/0077* (2013.01); *A61B 5/742* (2013.01); *G06T 7/70* (2017.01); *H04N 5/2353* (2013.01);
(Continued)

(58) Field of Classification Search
CPC .................. H04N 5/2353; G06T 7/70; G06T 2207/30201; A61B 5/0037; A61B 5/0077;
(Continued)

(56) References Cited

U.S. PATENT DOCUMENTS

| 5,305,759 A | 4/1994 | Kaneko et al. |
| 2015/0173618 A1 | 6/2015 | Kusukame |
| 2017/0332965 A1 | 11/2017 | Hasegawa et al. |

FOREIGN PATENT DOCUMENTS

| CN | 107865639 A | * | 4/2018 |
| JP | 4-189349 | | 7/1992 |

(Continued)

OTHER PUBLICATIONS

International Search Report of PCT application No. PCT/JP2018/025433 dated Sep. 18, 2018.

*Primary Examiner* — Robert Chevalier
(74) *Attorney, Agent, or Firm* — McDermott Will & Emery LLP

(57) ABSTRACT

A biological measuring device includes a light source that emits first light illuminating an area on a living body, an imaging device that detects second light returned from the living body and acquires a first image including at least part of the living body, and a control circuit that controls the light source. If a specific part of the living body is not located in a predetermined coordinate range in the first image, the control circuit restricts emission of the first light from the light source. The predetermined coordinate range is set outside the area.

14 Claims, 12 Drawing Sheets

(51) Int. Cl.
*G06T 7/70* (2017.01)
*H04N 5/235* (2006.01)
*A61B 5/026* (2006.01)

(52) U.S. Cl.
CPC .......... *A61B 5/0042* (2013.01); *A61B 5/0261* (2013.01); *A61B 5/486* (2013.01); *A61B 2562/0233* (2013.01); *G06T 2207/30201* (2013.01)

(58) Field of Classification Search
CPC ..... A61B 5/743; A61B 5/6803; A61B 5/0261; A61B 5/486; A61B 5/0042; A61B 5/742; A61B 5/18; A61B 5/004; A61B 5/1455; A61B 5/0295; A61B 2562/0233; A61B 2562/046; A61B 2560/0209
USPC ................................ 600/476, 477, 478, 479
See application file for complete search history.

(56) References Cited

FOREIGN PATENT DOCUMENTS

| | | |
|---|---|---|
| JP | 11-164826 | 6/1999 |
| JP | 2002-224092 | 8/2002 |
| JP | 2012-155917 | 8/2012 |
| JP | 5188786 B2 * | 4/2013 |
| JP | 2015-134157 | 7/2015 |
| JP | 2015-201452 | 11/2015 |
| JP | 2016-131604 A | 7/2016 |
| JP | 2017-124153 | 7/2017 |
| WO | 2016/084834 | 6/2016 |

\* cited by examiner

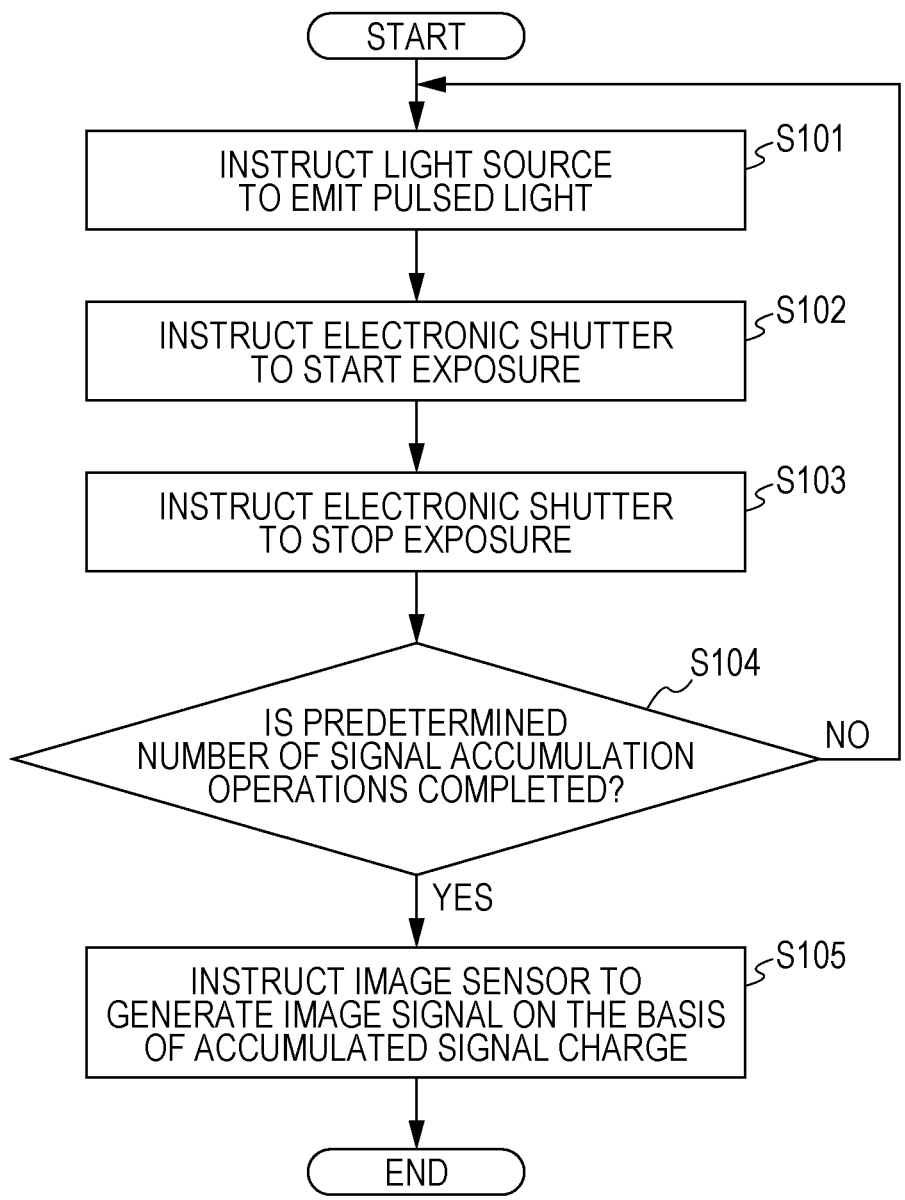

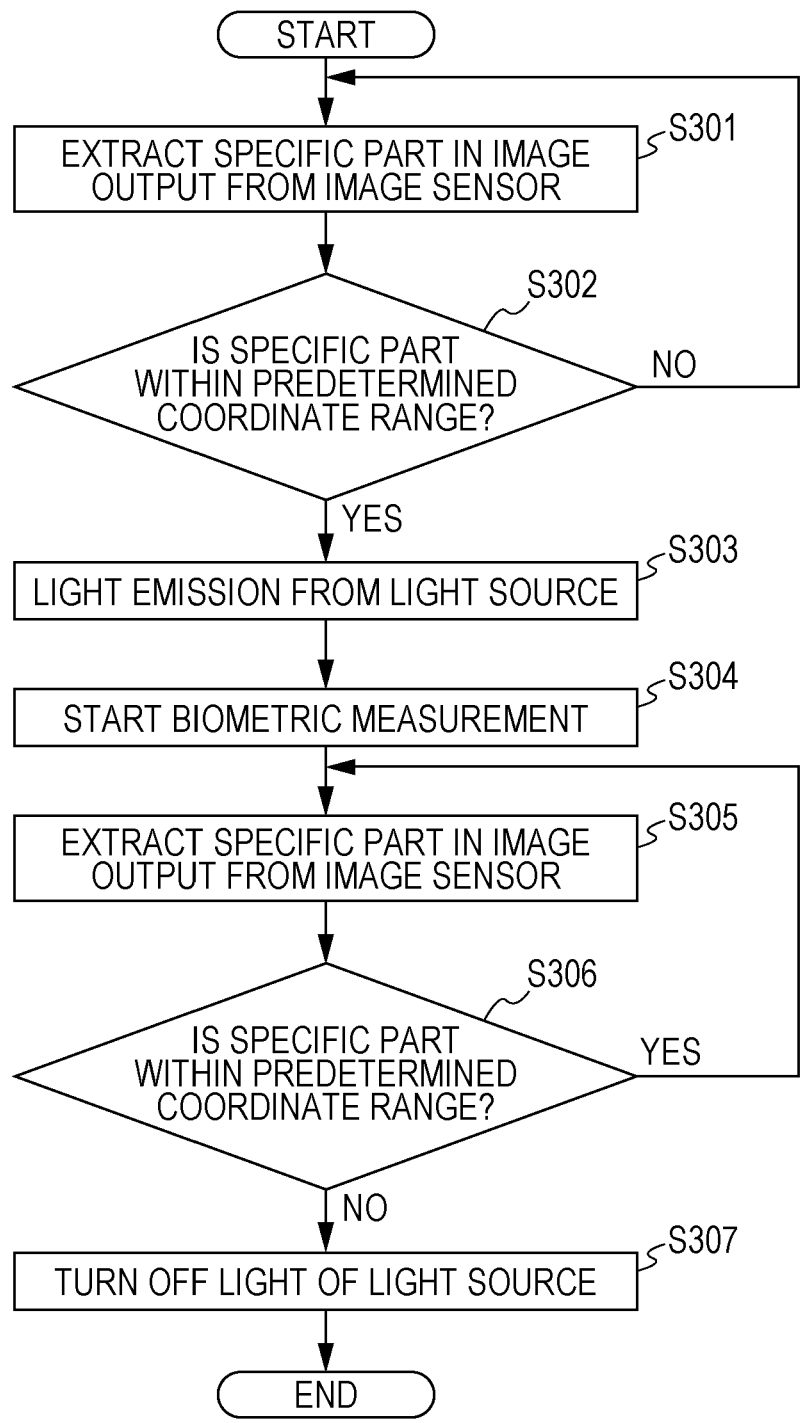

BIOLOGICAL MEASURING DEVICE AND HEAD MOUNTED DISPLAY APPARATUS

BACKGROUND

1. Technical Field

The present disclosure relates to a biological measuring device and a head mounted display apparatus.

2. Description of the Related Art

In the field of bioinstrumentation, a method is used in which information about the inside of a living body is acquired from information acquired from light emitted to the living body and transmitted through the inside of the living body. According to the method, a reflection component from the surface of the living body may be noise and cause a problem. To remove noise due to the surface reflection component and acquire only desired internal information, there is a known method described in, for example, Japanese Unexamined Patent Application Publication No. 11-164826. Japanese Unexamined Patent Application Publication No. 11-164826 describes a method for performing measurement by using a light source and a photodetector spaced apart from each other at a certain interval and in tight contact with a part to be measured.

SUMMARY

In one general aspect, the techniques disclosed here feature a biological measuring device including a light source that emits first light illuminating an area on a living body, an imaging device that detects second light returned from the living body and acquires a first image including at least part of the living body, and a control circuit that controls the light source. If a specific part of the living body is not located in a predetermined coordinate range in the first image, the control circuit restricts emission of the first light from the light source. The predetermined coordinate range is set outside the area.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1C is a flowchart illustrating an outline of operation performed by a control circuit;

FIG. 3 is a flowchart illustrating operation performed by the biological measuring device according to Embodiment 1;

DETAILED DESCRIPTION

Figure 1A:
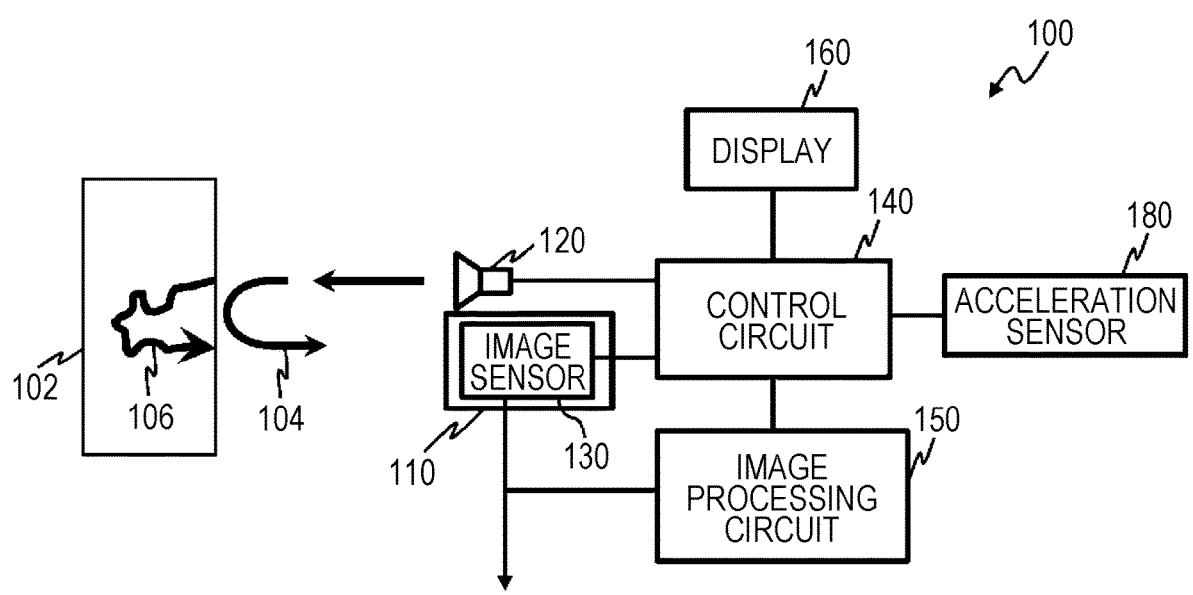
FIG. 1A is a schematic illustration of a biological measuring device according to Embodiment 1 and how the biological measuring device captures an image of an object.

The present disclosure includes a biological measuring device and a head mounted display apparatus described in the following items.

Item 1

A biological measuring device according to Item 1 of the present disclosure includes
  a light source that emits first light illuminating an area on a living body,
  an imaging device that detects second light returned from the living body and acquires a first image including at least part of the living body, and
  a control circuit that controls the light source.

If a specific part of the living body is not located in a predetermined coordinate range in the first image, the control circuit restricts emission of the first light from the light source. The predetermined coordinate range is set outside the area.

Item 2
  The biological measuring device according to Item 1 may further include
    an image processing circuit.
    The image processing circuit may determine whether the specific part of the living body is located in the predetermined coordinate range in the first image.
Item 3
  In the biological measuring device according to Item 1 or 2, if the specific part of the living body is not located in the predetermined coordinate range in the first image, the control circuit may cause the light source not to emit the first light. If the specific part is located in the predetermined coordinate range in the first image, the control circuit may cause the light source to emit the first light and acquire the biological information about the living body based on the second light detected by the imaging device.
Item 4
  In the biological measuring device according to Item 3, if the specific part moves from inside to outside of the predetermined coordinate range in the first image during acquisition of the biological information, the control circuit may cause the light source to reduce power of the first light or may cause the light source to stop emission of the first light.
Item 5
  In the biological measuring device according to any one of Items 1 to 4, if the specific part is not located in the predetermined coordinate range in the first image, the control circuit may further output a signal indicating that the specific part is not located in the predetermined coordinate range in the first image.
Item 6
  The biological measuring device according to any one of Items 1 to 5 may further include
    a display.
    The control circuit may cause the display to display the first image.
Item 7
  In the biological measuring device according to Item 6, if the specific part is not located in the predetermined coordinate range in the first image, the control circuit may cause the display to display a second image indicating that at least one selected from the group consisting of the position of the light source, the position of the biological measuring device, the orientation of the light source, and the orientation of the biological measuring device is to be changed.
Item 8
  In the biological measuring device according to any one of Items 1 to 7, the area on the living body may be included in the at least part of the living body.
Item 9
  In the biological measuring device according to any one of Items 1 to 8, the specific part may be at least one selected from the group consisting of the eyes, nose, mouth, ears, and eyebrows.
Item 10
  In the biological measuring device according to Item 2, the image processing circuit may further determine whether a target portion of the living body is located in the area in the first image. If the target portion is not located in the area in the first image, the control circuit may output a signal for warning.
Item 11
  In the biological measuring device according to Item 10, the target portion may be the forehead. The image processing circuit may calculate coordinates of the forehead in the first image and determine whether the coordinates of the forehead are in the area, and
    the control circuit may output the signal for warning if the coordinates of the forehead are not in the area.
Item 12
  The biological measuring device according to Item 11 may further include a display.
  If the coordinates of the forehead are not in the area, the control circuit may cause the display to display a third image indicating that at least one selected from the group consisting of the position of the light source, the position of the biological measuring device, the orientation of the light source, and the orientation of the biological measuring device is to be changed.
Item 13
  A biological measuring device according to Item 13 of the present disclosure includes
    a light source that emits first light illuminating an area on a living body,
    an imaging device that detects second light returned from the living body and acquires a first image including at least part of the living body, and
    a control circuit that controls the light source.
  If the position of the eyes of the living body overlaps the area in the first image, the control circuit restricts emission of the first light from the light source.
Item 14
  A head mounted display apparatus according to Item 14 of the present disclosure is a head mounted display apparatus wearable on the head of a living body.
  The head mounted display apparatus includes
    the biological measuring device according to any one of Items 1 to 13 and a display connected to the biological measuring device.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

Note that each of the embodiments below describes a general or specific example. A value, a shape, a material, a constituent element, and the arrangement positions of the constituent elements are only examples and shall not be construed as limiting the scope of the technology described in the present specification. In addition, among the constituent elements in the embodiments described below, the constituent element that does not appear in an independent claim, which has the broadest scope, is described as an optional constituent element.

Embodiments are described in detail below with reference to the accompanying drawings.

Embodiment 1

1. Biological Measuring Device

Figure 1B:
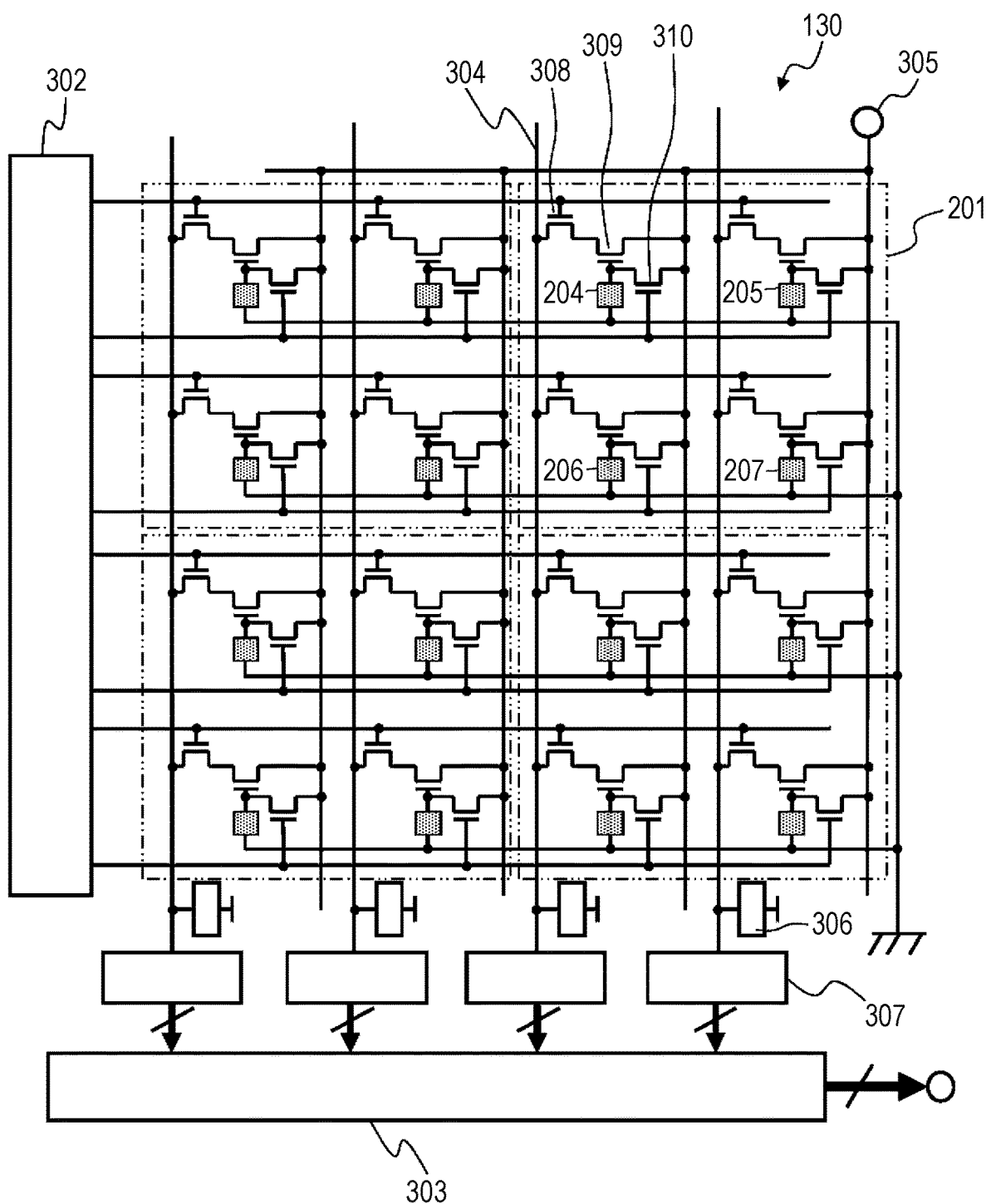
FIG. 1B is a diagram illustrating an example of the configuration of an image sensor.
Figure 2:
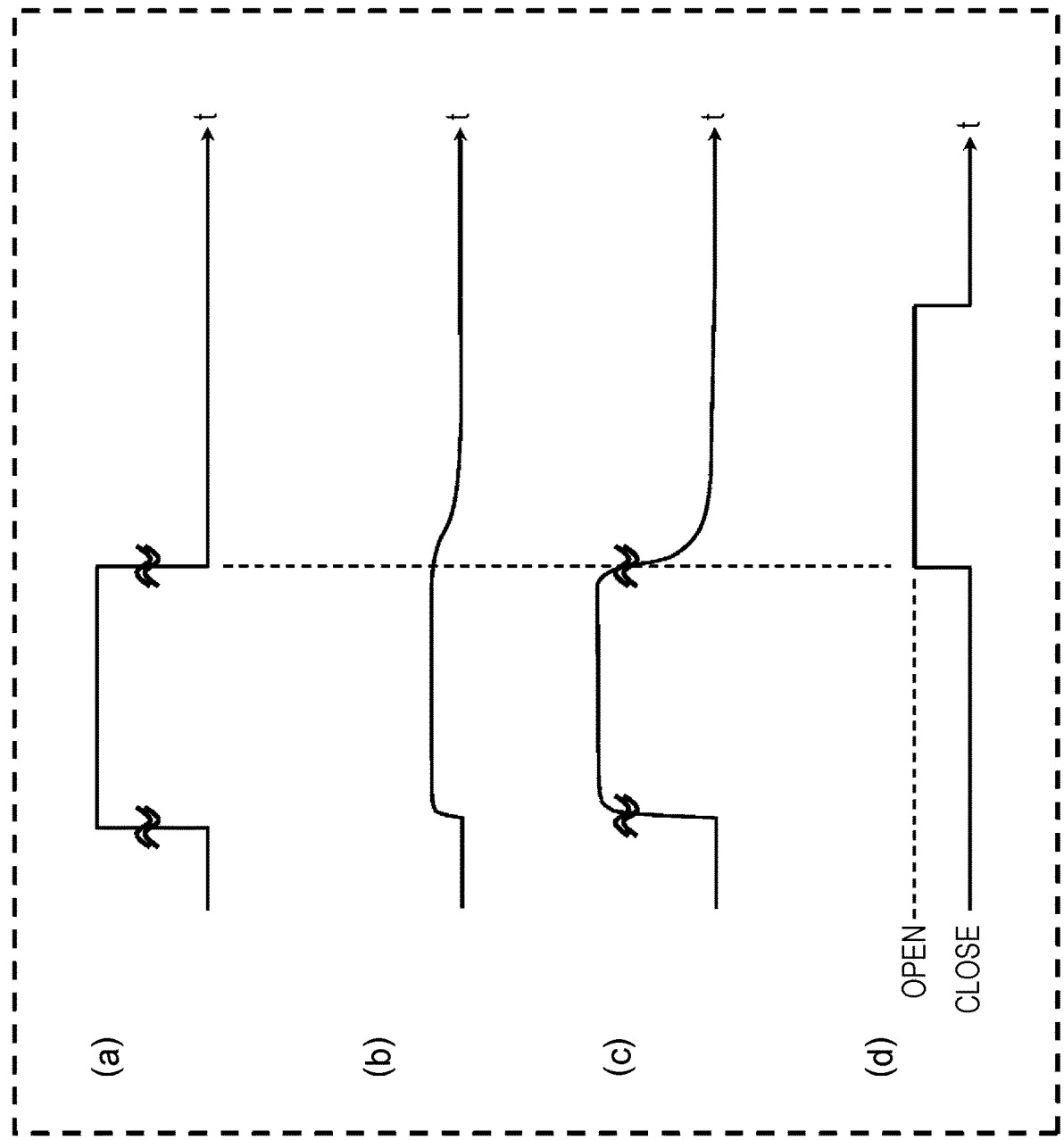
FIG. 2 illustrates operation timing of an optical signal of a surface reflection component reflected by a surface of the object, an optical signal of an internal scattering component scattered inside the object, an optical signal obtained by combining the surface reflection component with the internal scattering component, and an electronic shutter in the biological measuring device according to Embodiment 1.

The configuration of a biological measuring device 100 according to Embodiment 1 is described first with reference to FIGS. 1A to 2.

FIG. 1A is a schematic illustration of the biological measuring device 100 according to the present embodiment. The biological measuring device 100 according to the present embodiment is a device that measures internal information of an object 102 that is a living body. A target portion of the object 102 is a part of a living body (for example, the human body) and is, for example, a part having a skin that is not covered by hair. The target portion can be, for example, a human forehead. When the target portion is a forehead, the biological measuring device 100 can acquire information regarding the activity state of cerebral blood flow.

The biological measuring device 100 includes a light source 120, an imaging device 110, a control circuit 140, an image processing circuit 150, a display 160, and an acceleration sensor 180. The imaging device 110 includes an image sensor 130. The light source 120 and the image sensor 130 are disposed adjacent to each other. The control circuit 140 is electrically connected to the light source 120, the image sensor 130, the image processing circuit 150, the display 160, and the acceleration sensor 180. The control circuit 140 controls the light emission timing of the light source 120 and the light detection timing of the image sensor 130. The light source 120 emits first light (for example, infrared light or visible light) toward the object 102. The imaging device 110 detects second light returned from the object 102. The second light is light reflected by the object 102 or scattered within the object 102. In addition, the imaging device 110 acquires a first image that is an image including at least part of the object 102. These functions of the imaging device 110 are provided by the image sensor 130. The image sensor 130 detects the second light and outputs an image signal. The image processing circuit 150 determines whether the position and tilt of the object 102 are appropriate for the illumination range of the first light emitted from the light source 120 on the basis of the image signal output from the image sensor 130. The control circuit 140 controls the light emission of the light source 120 on the basis of the result of determination. The display 160 displays the result of measurement of the internal information of the object 102. The acceleration sensor 180 detects the movement of the biological measuring device 100.

More specifically, the image processing circuit 150 analyzes the image signal output from the image sensor 130 and determines whether at least one specific part of the object 102 exists within a predetermined coordinate range in the first image. For example, if the target portion is a human face, the specific part may be a part that is individual to each person, such as the eyes, nose, mouth, ears, or eyebrows. The image processing circuit 150 determines, by image recognition, whether the specific part is at an appropriate position in the image and outputs a signal indicating the result of determination. The control circuit 140 turns on or off light emission from the light source 120 or controls the power of the first light emitted from the light source 120 in accordance with whether the specific part of the object 102 is included in a specific area of the first image on the basis of the signal. If the specific part is not located within the predetermined coordinate range, the control circuit 140 limits the emission of the first light by the light source 120. For example, the control circuit 140 instructs the light source 120 not to emit the first light if the specific part is not located within the coordinate range. However, the control circuit 140 instructs the light source 120 to emit the first light if the specific part is located within the coordinate range. More specifically, the control circuit 140 does not allow the light source 120 to emit light if none of characteristic parts, such as the human eyes, nose, mouth, ears, and eyebrows, to be measured is within a predetermined range of the first image. However, the control circuit 140 allows the light source 120 to emit light if at least one of characteristic parts, such as the human eyes, nose, mouth, ears, and eyebrows, to be measured is within the predetermined range of the first image.

With such a configuration, even after a measurement instruction is issued from the user, the light source 120 emits light only when the position and tilt of the object 102 are in an appropriate state. Accordingly, the power consumption of the biological measuring device 100 can be reduced as compared with the configuration in which the light emission mode is always set to ON after a measurement instruction is issued. In addition, for example, light emitted from the light source 120 can be prevented from entering the human eye, which is an object to be measured.

The configuration according to the present embodiment is described in more detail below.

1-1. Light Source

The light source 120 emits light to the object 102. The light emitted from the light source 120 reaches the object 102 and changes to surface reflection components 104, which are components reflected by a surface of the object 102, and internal scattering components 106, which are components that are reflected once or scattered or multiply scattered inside the object 102. The surface reflection components 104 include three components, that is, a direct reflection component, a diffuse reflection component, and a scatter reflection component. The direct reflection component is a reflection component having an incident angle and a reflection angle that are the same. The diffuse reflection component is a component that is diffused and reflected by the irregularity of the surface. The scatter reflection component is a component that is scattered and reflected by the internal tissues in the vicinity of the surface. If the target portion is a human forehead, the scatter reflection component is a component that is scattered and reflected inside the epidermis. Hereinafter, the present disclosure is described with reference to the surface reflection components 104 that include these three components and the internal scattering components 106 that do not include a scatter reflection component.

The surface reflection component 104 and the internal scattering component 106 change their traveling directions due to reflection or scattering, and some of the components reach the image sensor 130. The light source 120 follows the instruction from the control circuit 140 and generates pulsed light at predetermined time intervals or a plurality of times (at predetermined time points). The pulsed light generated by the light source 120 can be, for example, a square wave with fall time close to zero. The fall time refers to the time from when the power of the pulsed light starts to decrease from the peak value to when the power reaches almost zero.

In general, the spread of the rear end of the internal scattering component 106 in the object 102 is about 4 ns. In consideration of the value, the fall time of the pulsed light simply needs to be less than or equal to, for example, 2 ns, which is half the value. It is more effective if the fall time is set to be less than or equal to 1 ns, which is half of 2 ns. The waveform of the pulsed light need not be exactly square. The pulsed light generated by the light source 120 may have any rise time. This is because in the measurement using the biological measuring device according to the embodiment of the present disclosure (described below), on the time axis of the pulsed light, a portion of the pulsed light in which the power thereof is falling is used, and a portion in which the power thereof is rising is not used. For example, the light source 120 may be a laser light source, such as an LD. A power rising portion of a pulsed wave of an LD is at a substantially right angle with respect to the time axis, and an LD has a rapid time response characteristic.

The wavelength of the light source 120 may be set to, for example, a value greater than or equal to 650 nm and less than or equal to 950 nm. This wavelength range is included in the wavelength range of red to near infrared. This is because this wavelength band is a wavelength band in which light can easily be transmitted to the inside of the object 102. As used herein, the term "light" refers to not only visible light but infrared light.

The biological measuring device 100 according to the present disclosure measures the object 102 in a non-contact manner. Accordingly, if the target portion of the object 102 is a human forehead, the power of light emitted from the light source is set to a value such that the influence of the light does not affect the retina. For example, the power of light emitted from the light source can be set so as to meet Class 1 of the laser safety standard defined by each of countries. In this case, light having such a low illuminance that the allowable exposure limit AEL is less than 1 mW is emitted to the object 102. However, the light source 120 itself need not always meet Class 1. For example, an optical element, such as a diffuser or an ND filter, may be mounted in front of the light source 120 so that the light is diffused or attenuated to meet the laser safety standard Class 1.

For example, a streak camera in the related art described in Japanese Unexamined Patent Application Publication No. 4-189349 has been used to distinguish and detect information (for example, the absorption coefficients or scattering coefficients) at different locations in the depth direction inside the living body. Therefore, to perform measurement with a desired spatial resolution, an ultrashort pulse of light having a pulse width of femtosecond or picosecond has been used. In contrast, according to the present embodiment, the biological measuring device 100 is used to distinguish between the surface reflection component 104 and the internal scattering component 106 for detection. Accordingly, the pulsed light emitted from the light source 120 need not be an ultrashort pulse of light, and the pulse width may be any value. When light is emitted onto the forehead to measure a cerebral blood flow, the amount of the internal scattering components 106 is very small, from one several thousandth to one several ten thousandth of the amount of the surface reflection components 104. Furthermore, in consideration of the laser safety standards, the amount of light that can be emitted is small, and it is considerably difficult to detect the internal scattering component 106. Accordingly, the light source 120 generates pulsed light having a relatively large pulse width so as to increase the accumulated amount of the internal scattering components 106 with a time delay and increase the detected amount of light. In this manner, the SNR can be improved.

For example, the light source 120 emits pulsed light having a pulse width greater than or equal to 3 ns. Alternatively, the light source 120 may emit pulsed light having a pulse width greater than or equal to 5 ns. Still alternatively, the light source 120 may emit pulsed light having a pulse width greater than or equal to 10 ns. Note that if the pulse width is excessively large, light that is not used increases and is wasted. Accordingly, the light source 120 generates pulsed light having a pulse width less than or equal to 50 ns, for example. Alternatively, the light source 120 may emit pulsed light having a pulse width less than or equal to 30 ns or a pulse width less than or equal to 20 ns.

The emission pattern of the light from the light source 120 may be a pattern having a uniform power distribution over the illumination area, for example. This is because unlike the method described in, for example, Japanese Unexamined Patent Application Publication No. 11-164826, the biological measuring device 100 according to the present embodiment employs a method that temporally separates and reduces the surface reflection components 104. According to the method described in Japanese Unexamined Patent Application Publication No. 11-164826, the detector and the light source are disposed so as to be spaced apart by 3 cm, and the surface reflection components 104 are spatially reduced. Thus, the light needs to be discretely emitted. In contrast, according to the present embodiment, the surface reflection components 104 are temporally separated and are reduced. Thus, the internal scattering component 106 can be detected even at a Null point immediately below the emission point on the object 102. Accordingly, to increase the measurement resolution, the light having spatially uniform power can be emitted over the entire surface of the object 102.

1-2. Image Sensor

The image sensor 130 receives the light returned from the object 102. The image sensor 130 has a plurality of pixels, which are a plurality of light detection cells arranged two-dimensionally, and acquires two-dimensional information about the object 102 at a time. The image sensor 130 can be, for example, a CCD image sensor or a CMOS image sensor.

The image sensor 130 has an electronic shutter. The electronic shutter is a circuit that controls accumulation and discharge of signal charges generated through photoelectric conversion. The electronic shutter controls the length of one electrical charge accumulation period for which the received light is converted into an effective electrical signal and a time length from the end of one electrical charge accumulation period to the start of the next electrical charge accumulation period. In the following description, the length of the electrical charge accumulation period is referred to as a "shutter width", and the time length from the end of one electrical charge accumulation period to the start of the next electrical charge accumulation period is referred to as a "shutter timing". In addition, the state in which the image sensor 130 is accumulating electrical charges is referred to a state in which the electronic shutter is "OPEN (an open state)", and the state in which the image sensor 130 has stopped accumulating electrical charges is referred to as a state in which the electronic shutter is "CLOSE (a closed state)".

The image sensor 130 can control the shutter timing within the range of sub-nanoseconds, for example, the range of 30 ps to 1 ns by using the electronic shutter. A TOF camera in the related art intended for distance measurement detects all of the pulsed light emitted from the light source 120 and reflected by an object to correct the influence of the luminance of the object. Accordingly, a TOF camera in the related art needs to have a shutter width greater than the pulse width of the pulsed light. In contrast, the biological measuring device 100 according to the present embodiment need not correct the amount of light coming from the object. Consequently, the shutter width need not be greater than the pulse width of the pulsed light and can be, for example, about 1 to about 30 ns. According to the biological measuring device 100 of the present embodiment, since the shutter width can be reduced, the dark current included in the detection signal can be reduced.

If the target portion is a human forehead and the information, such as cerebral blood flow, is detected, the attenuation factor of light inside the forehead is significantly large. For example, the attenuation factor may be about one millionth. Accordingly, to detect the internal scattering component 106, the amount of light obtained through only one pulse emission may be insufficient. In particular, when performing emission that meets Class 1 of the laser safety standard, the amount of light is significantly small. In this case, the light source 120 emits pulsed light a plurality of times within one frame, and the image sensor 130 accumulates electrical charge a plurality of times by the electronic shutter in accordance with the emission. In this manner, the detection signals are accumulated, and the sensitivity is increased. For example, it is assumed that 11-ns pulsed light is uniformly emitted from the light source 120 to the entire target portion of the object 102 through a diffuser at 30 Fps 128,000 times per frame. In that case, under the condition that meets Class 1, the driving power per laser diode is about 180 mW. If the capacity of the battery is, for example, 3000 mAh and four laser diodes are provided in the biological measuring device 100, the laser diodes are driven by the battery only for about 4.2 hours, despite considering only the driving power of the light source.

Accordingly, the biological measuring device 100 according to the present embodiment turns off the light source 120 that consumes much power if the object 102 is not located at an appropriate position and does not have tilt suitable for biometric measurement. The biological measuring device 100 turns on the light source 120 only when the object 102 is under the condition suitable for biometric measurement. In this manner, the biological measuring device 100 can perform biometric measurement with a high SNR while reducing power consumption.

A configuration example of the image sensor 130 is described below.

The image sensor 130 has a plurality of pixels which are a plurality of photodetection cells arranged two-dimensionally on an imaging surface. Each of the pixels has a light receiving element, such as a photodiode.

FIG. 1B is a diagram illustrating an example of the configuration of the image sensor 130. In FIG. 1B, a region surrounded by an alternate long and two short dashes line corresponds to one of pixels 201. The pixel 201 includes one photodiode. In FIG. 1B, only four pixels arranged in two rows and two columns are illustrated. Note that in reality, a larger number of pixels are arranged.

The pixel 201 includes a photodiode, a source follower transistor 309 that is an amplifying transistor, a row selection transistor 308, and a reset transistor 310. Each of the transistors is, for example, a field effect transistor formed on a semiconductor substrate. However, the transistors are not limited thereto. As illustrated in FIG. 1B, one of input and output terminals of the source follower transistor 309 (typically the source) and one of input and output terminals of the row selection transistor 308 (typically the drain) are connected to each other. A gate that is a control terminal of the source follower transistor 309 is connected to a photodiode. A hole or electron, which is signal charge generated by the photodiode, is stored in a floating diffusion layer that is an electrical charge accumulation node between the photodiode and the source follower transistor 309 and that functions as a charge accumulation unit.

Although not illustrated in FIG. 1B, a switch may be provided between the photodiode and each of floating diffusion layers 204, 205, 206, and 207. This switch switches the conduction state between the photodiode and the floating diffusion layer in accordance with a control signal received from the control circuit 140. In this manner, the start and stop of the accumulation of signal charges in the floating diffusion layer are controlled. The electronic shutter according to the present embodiment has a mechanism for controlling the above-described charge accumulation.

The signal charge accumulated in the floating diffusion layer is read out when the gate of the row selection transistor 308 is turned on by a row selection circuit 302. At this time, a current flowing from a source follower power source 305 to the source follower transistor 309 and a source follower load 306 is amplified in accordance with the signal potential of the floating diffusion layer. An analog signal based on this current read from a vertical signal line 304 is converted into digital signal data by an analog-digital (AD) conversion circuit 307 connected to each of the columns. The digital signal data is read out for each of the columns by a column selection circuit 303 and is output from the image sensor 130. The row selection circuit 302 and the column selection circuit 303 read out data for one row and, thereafter, read out data for the next row. In the same manner, the row selection circuit 302 and the column selection circuit 303 read out signal charge information in the floating diffusion layers for all rows. After reading out all signal charges, the control circuit 140 turns on the gate of the reset transistor 310 to reset all the floating diffusion layers. In this manner, imaging of one frame is completed. Thereafter, by repeating high-speed imaging of frames in the same manner, imaging of a series of frames performed by the image sensor 130 is completed.

While the present embodiment has been described with reference to an example of the CMOS image sensor 130, an imaging device may be of a CCD type or a single photon counting type. Alternatively, an imaging device may be an amplifying image sensor (EMCCD, ICCD).

1-3. Control Circuit and Image Processing Circuit

The control circuit 140 controls the time difference (that is, the phase difference) between the light emission timing of the pulsed light from the light source 120 and the shutter timing of the image sensor 130. The term "light emission timing" of the light source 120 refers to a point in time when the power of the pulsed light emitted by the light source 120 starts rising. The control circuit 140 may control the phase difference by changing the light emission timing or may control the phase difference by changing the shutter timing.

The control circuit 140 may be configured to remove an offset component from the signal detected by the light receiving element of the image sensor 130. The offset component is a signal component generated by environment light, such as sunlight or fluorescent light, or a signal component generated by ambient light. If the image sensor 130 detects a signal with the light source 120 not emitting light, that is, with driving of the light source 120 turned off, the offset component generated by the environment light or the ambient light can be estimated.

The control circuit 140 may be an integrated circuit including a processor, such as a central processing unit (CPU) or a microcomputer, and a memory, for example. The control circuit 140 performs various processes, such as control of the light emission timing and shutter timing, estimation of the offset component, and removal of the offset component, by executing a program stored in the memory.

The image processing circuit 150 is an arithmetic circuit that performs arithmetic operations, such as image processing based on a signal output from the image sensor 130. The arithmetic circuit can be built by a combination of a programmable logic device (PLD), such as a digital signal processor (DSP) or a field programmable gate array (FPGA), a central processing unit (CPU), or a graphics processing unit (GPU) and a computer program. Note that the control circuit 140 and the image processing circuit 150 need not be separated into individual circuits, but may be a single circuit formed by integrating the control circuit 140 and the image processing circuit 150.

FIG. 1C is a flowchart illustrating an outline of the operation performed by the control circuit 140. The control circuit 140 performs the operation schematically illustrated in FIG. 1C (the details are described later). The control circuit 140 instructs the light source 120 to emit pulsed light for a predetermined period of time first (step S101). At this time, the electronic shutter of the image sensor 130 is in a state in which charge accumulation is stopped. The control circuit 140 instructs the electronic shutter to stop accumulation until the end of the period of time for which part of the pulsed light is reflected by the surface of the object 102 and reaches the image sensor 130. Subsequently, at a timing when other part of the pulsed light is scattered inside the object 102 and reaches the image sensor 130, the control circuit 140 instructs the electronic shutter to start accumulating electrical charges, that is, start exposure (step S102). After a predetermined period of time has elapsed, the control circuit 140 instructs the electronic shutter to stop electrical charge accumulation (step S103). The exposure start timing and exposure stop timing are determined in advance through experiments or numerical calculation. If the distance between the light source 120 and the object 102 is known, the period of time from when light is emitted from the light source 120 to when the light reaches the image sensor 130 can be calculated. Accordingly, for example, control can be performed so that exposure is performed only during a period of time for which the rear end portion of the light pulse enters the image sensor 130. Subsequently, the control circuit 140 determines whether the number of times the above-described signal accumulation has been performed has reached a predetermined number (step S104). If the determination is No, steps S101 to S103 are repeated until the determination changes to Yes. If in step S104, the determination is Yes, the control circuit 140 instructs the image sensor 130 to generate and output a signal indicating an image based on the signal charge accumulated in each of the floating diffusion layers (step S105). The image of one frame is formed through the operation illustrated in FIG. 1C. By repeating the series of operations a plurality of times, a moving image is obtained.

Through the above-described operations, a component of light scattered inside the object to be measured can be detected with high sensitivity. Note that multiple times of light emission and electrical charge accumulation are not essential and are performed as needed.

1-4. Others

The biological measuring device 100 may include imaging optics that form a two-dimensional image of the object 102 on the light receiving surface of the image sensor 130. The optical axis of the imaging optics is substantially orthogonal to the light receiving surface of the image sensor 130. The imaging optics may include a zoom lens. If the position of the zoom lens changes, the magnification of the two-dimensional image of the object 102 changes, and the resolution of the two-dimensional image on the image sensor 130 changes. Thus, even when the distance to the object 102 is long, the area to be measured can be enlarged and observed in detail.

In addition, the biological measuring device 100 may include a bandpass filter disposed between the object 102 and the image sensor 130. The bandpass filter allows only light in the wavelength band of light emitted from the light source 120 or in a wavelength band close to the wavelength band to pass therethrough. In this manner, the influence of a disturbance component, such as environment light, can be reduced. The bandpass filter is formed with, for example, a multilayer filter or an absorption filter. In consideration of a band shift due to the temperature of the light source 120 or a band shift in accordance with oblique incidence to the filter, the bandwidth of the bandpass filter may be in the range of about 20 to about 100 nm.

The biological measuring device 100 may include a polarizer disposed between the light source 120 and the object 102 and a polarizer disposed between the image sensor 130 and the object 102. In this case, the polarizer disposed adjacent to the light source 120 and the polarizer disposed adjacent to the image sensor may be arranged such that the polarization directions thereof are in a relationship of crossed Nicols. In this manner, among the surface reflection components 104 from the object 102, arrival of a regular reflection component, that is, a component having the same incident angle and reflection angle at the image sensor 130 can be prevented. That is, the amount of light when the surface reflection components 104 reach the image sensor 130 can be reduced.

2. Operation

The biological measuring device 100 according to the present disclosure identifies and detects the internal scattering component 106 from the surface reflection component 104. When the target portion is a human forehead, the power of the signal of the internal scattering component 106 to be detected is significantly small. This is because, as described above, a significantly small amount of light that meets the safety standards of laser light is emitted and, in addition, the scattering and absorption of light by the scalp, cerebrospinal fluid, skull, gray matter, white matter, and blood flow are large. Furthermore, a change in the signal power due to a change in the blood flow volume or the component in the blood flow during the brain activity is one several tenth of the signal power, which is significantly small. Accordingly, the imaging is performed while avoiding the surface reflection component 104 being mixed into the detection signal, since the surface reflection component 104 has power which is several thousand to tens of thousands times the power of the signal component to be detected.

The operation performed by the biological measuring device 100 according to the present embodiment is described below.

As illustrated in FIG. 1A, when the light source 120 emits pulsed light to the object 102, the surface reflection components 104 and the internal scattering components 106 are generated. Some of the surface reflection components 104 and some of the internal scattering components 106 arrive at the image sensor 130. Since the internal scattering component 106 passes through the inside of the object 102 during a period of time from when the internal scattering component 106 is emitted from the light source 120 to when the internal scattering component 106 reaches the image sensor 130, the optical path length is longer than that of the surface reflection component 104. Consequently, on average, the internal scattering components 106 arrive at the image sensor 130 later than the surface reflection components 104.

FIG. 2 is a diagram illustrating a signal of light returned from the object 102 to the image sensor 130 when square pulse light is emitted from the light source 120. The abscissa represents time (t) for signals (a) to (d), and the ordinate for the signals (a) to (c) represents the signal power. The ordinate for the signal (d) indicates the OPEN or CLOSE state of the electronic shutter. The signal (a) represents the surface reflection component 104. The signal (b) represents the internal scattering component 106. The signal (c) represents a combined component of the signal (a) representing the surface reflection component 104 and the signal (b) representing the internal scattering component 106. As can be seen from the signal (a), the surface reflection component 104 remains square. In contrast, as can be seen from the signal (b), since the internal scattering component 106 is the sum of the light rays that have traveled various optical path lengths, the internal scattering component 106 exhibits a characteristic such that the rear end of the pulsed light has a trail behind it. That is, the fall time period of the internal scattering component 106 is longer than that of the surface reflection component 104. To increase the ratio of the internal scattering component 106 in the signal (c) and extract the internal scattering components 106 from the signal (c), the electronic shutter simply starts charge accumulation after the rear end of the surface reflection component 104, that is, when the waveform or the power of the surface reflection component 104 falls or thereafter, as indicated by the signal (d). This shutter timing is controlled by the control circuit 140. As described above, the biological measuring device 100 according to the present disclosure only needs to be able to distinguish and detect the internal scattering component 106 from the surface reflection component 104 and, thus, the emission pulse width and the shutter width may be any values. As a result, unlike a method in the related art using a streak camera, the biological measuring device 100 can be achieved with a simple configuration, and the cost can be significantly reduced.

In the example of the signal (a) illustrated in FIG. 2, the rear end of the pulse of the surface reflection component 104 falls vertically. In other words, the time from when the surface reflection component 104 starts falling to when it stops falling is zero. However, in reality, in some cases, the falling edge of the pulsed light emitted from the light source 120 is not completely vertical, the surface of the object 102 has fine irregularities, or the surface reflection component 104 is scattered due to scattering in the epidermis. Accordingly, the trailing edge of the pulse does not fall vertically at all times. In addition, since the object 102 is generally an opaque object, the amount of light of the surface reflection component 104 is much larger than that of the internal scattering component 106. Consequently, even when the trailing edge of the pulse of the surface reflection component 104 slightly runs over the vertical falling position, the internal scattering component 106 disappears, which is problematic. Furthermore, an ideal binary electronic shutter operation as indicated by the signal (d) illustrated in FIG. 2 may not be provided due to a time delay associated with transfer of an electron during the readout period of the electronic shutter.

Therefore, the control circuit 140 may slightly delay the shutter timing of the electronic shutter so that the shutter timing is immediately after the fall of the surface reflection component 104. In consideration of the accuracy of the electronic shutter, the delay time may be longer than or equal to, for example, 1 ns. Note that the control circuit 140 may control the light emission timing of the light source 120 instead of controlling the shutter timing of the electronic shutter. The control circuit 140 can control the time difference between the shutter timing of the electronic shutter and the light emission timing of the light source 120. Note that when a change in blood flow volume or a blood flow component during brain activity is measured in a non-contact manner and if the shutter timing is delayed excessively, the internal scattering component 106 that is originally small is further reduced. Such a problem can be avoided by keeping the shutter timing in the vicinity of the rear end of the pulse of the surface reflection component 104. Because the time delay due to scattering by the object 102 is about 4 ns, the maximum amount of delay of the shutter timing can be set to about 4 ns.

The light amount of the internal scattering components 106 may be amplified by causing the light source 120 to emit pulsed light a plurality of times and accumulating the electrical charges a plurality of times at the same phase shutter timing for all the pulsed light.

Instead of placing a bandpass filter between the object 102 and the image sensor 130 or in addition to placing the bandpass filter, the control circuit 140 may estimate the offset component by performing an imaging operation for the same charge accumulation time period without instructing the light source 120 to emit light. The estimated offset component is difference-removed from the signal detected by the light receiving element of the image sensor 130. As a result, a dark current component generated in the image sensor 130 can be removed.

FIG. 3 is a flowchart illustrating the operation performed by the biological measuring device 100 according to Embodiment 1. After receiving a measurement start instruction (start) from the user, the imaging device 110 of the biological measuring device 100 captures the image of the object 102 and outputs an image signal. The image capture and image signal output can be performed continuously for each of frames, for example. The image processing circuit 150 extracts at least one specific part from the obtained image (step S301). At this time, since an image can be acquired on the basis of outside light, the light source 120 need not emit light. At this time, if the biological measuring device 100 includes a bandpass filter that transmits only light having a wavelength the same as the light emission wavelength of the light source 120, the detected light amount tends to be small. Accordingly, to acquire an image by using the image sensor 130 when the light source 120 is turned off, electrical charge may be continuously accumulated within one frame, instead of using an intermittent charge accumulation technique which is used in biometric measurement. By performing a continuous charge accumulation technique, the detected amount of light can be increased even when the light source 120 is turned off. However, if the near-infrared light component included in the outside light is still small, the amount of detected light is excessively small, which may make extraction of a specific part by the image processing circuit 150 difficult. In this case, the control circuit 140 may instruct the light source 120 to perform dummy light emission. In the dummy light emission, pulsed light need not be emitted. If continuous light is emitted, the detected amount of light increases.

The specific part may be a characteristic part, such as the eyes, nose, mouth, or eyebrows of the object. If the image processing circuit 150 recognizes at least one predetermined specific part in the image, the image processing circuit 150 determines whether the position of the part is within a predetermined coordinate range in the image (step S302). That is, the image processing circuit 150 determines whether the specific part (for example, eyes, nose, mouth, eyebrows, or forehead) is located at a predetermined position in the image. If the image processing circuit 150 determines that the specific part is located at a predetermined position, the control circuit 140 instructs the light source 120 to start light emission (step S303). However, if the image processing circuit 150 determines that the specific part is not detected or the specific part is not located within the predetermined coordinate range, the image processing circuit 150 continues to extract a specific part. The image processing circuit 150 periodically repeats extraction of the specific part until it determines that the specific part is within a predetermined area.

The timing at which the specific part is to be extracted may be a timing when the movement of the biological measuring device 100 or a specific tilt of the biological measuring device 100 itself is detected by the acceleration sensor 180 included in the biological measuring device 100. If the movement or tilt of the biological measuring device 100 occurs, the target portion (the forehead in this example) of the object 102 may be out of the illumination range of the light source 120 and the image range to be captured by the image sensor 130. Accordingly, the movement or tilt of the biological measuring device 100 is measured by the acceleration sensor 180 during the measurement. If the magnitude of the movement or tilt exceeds a predetermined value, steps S301 and S302 may be executed. In this manner, it can be efficiently determined whether the specific part is at the predetermined position without any waste.

After the light source 120 starts emitting light, the control circuit 140 starts biometric measurement of the object 102 (step S304). As described above, the biometric measurement is performed by controlling the light detection timing of the image sensor 130 in synchronization with the light emission timing of the light source 120. The image sensor 130 acquires an image indicating a two-dimensional distribution of light components that have entered the inside of the object 102 and have returned. The image indicates the internal characteristics of the object 102, such as the activity state of the cerebral blood flow in the object 102.

During the biometric measurement, the image processing circuit 150 periodically extracts a specific part from the image output from the image sensor 130 and makes the above-described determination (steps S305 and S306). If the image processing circuit 150 determines that the specific part is not located at a predetermined position in the image during the biometric measurement, the control circuit 140 instructs the light source 120 to turn off light (step S307). As a result, when the position of a specific part, such as the eyes, deviates from a position where it is expected during biometric measurement, the light source can turned off light and, thus, power consumption can be reduced. After the light source turns off light, the control circuit 140 may instruct the display 160 to display a warning indicating that the position of the specific part has deviated from the expected position. When seeing the display, a user can solve the problem, such as adjusting the position of the biological measuring device 100. After the processing in step S307, the processing performed by the biological measuring device 100 may proceed to step S301, where the biological measuring device 100 may perform the series of operations illustrated in FIG. 3 again.

According to the present embodiment, both extraction of the specific part on the basis of the image of the object 102 and determination regarding deviation of the specific part can be performed using the image sensor 130 for the biometric measurement. As a result, the biological measuring device 100 can be made compact, and the manufacturing cost can be reduced. By performing the processing presented in the flowchart illustrated in FIG. 3, the light source 120 can turned on light only as needed. As a result, the power consumed by the biological measuring device 100 can be reduced.

A relationship among the illumination area by the light source 120, the detection area by the image sensor 130, and the extraction area of a specific part is described below with reference to FIGS. 4A to 4C.

Figure 4A:
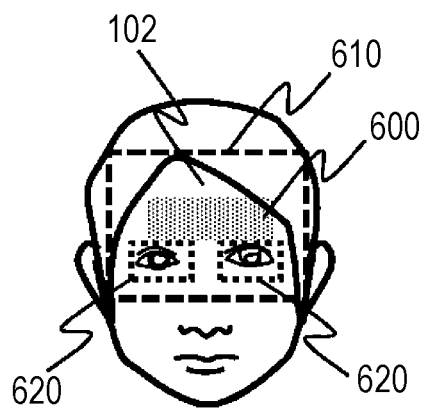
FIG. 4A is a diagram illustrating an example of an illumination area on the object by a light source of the biological measuring device, a detection area by the image sensor, and a specific part extraction area.
Figure 4B:
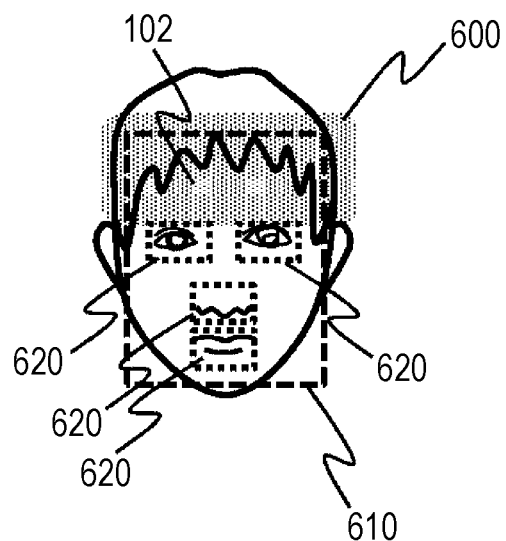
FIG. 4B is a diagram illustrating another example of an illumination area on the object by the light source of the biological measuring device, a detection area by the image sensor, and a specific part extraction area.
Figure 4C:
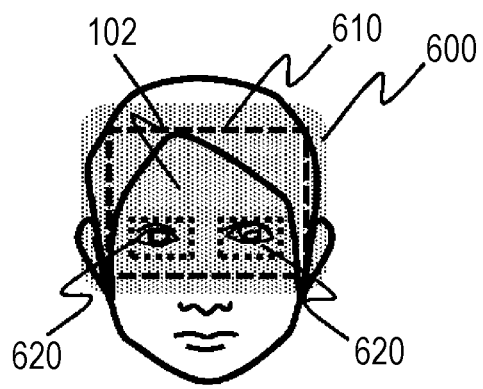
FIG. 4C is a diagram illustrating still another example of an illumination area on the object by the light source of the biological measuring device, a detection area by the image sensor, and a specific part extraction area.

FIGS. 4A to 4C are diagrams illustrating examples of an illumination area 600 by the light source 120, a detection area 610 by the image sensor 130, and a specific part extraction area 620. The illumination area 600 corresponds to an area of the object 102 onto which light is emitted from the light source 120. The image sensor 130 detects light returned from the detection area 610 of the object 102. The detection area 610 corresponds to an area of the object 102 included in the image acquired by the image sensor 130. The specific part extraction area 620 is an area where the specific part is to be located during the measurement of the living body in the image of the object 102 acquired by the image sensor 130. The specific part extraction area 620 corresponds to the predetermined coordinate range according to the present disclosure. In any of the examples, the specific part extraction area 620 is located inside the detection area 610 by the image sensor 130. However, the illumination area 600 by the light source 120 may be included in the detection area 610 (FIG. 4A) or may extend from the inside to the outside of the detection area 610 (FIGS. 4B and 4C).

If the power of light from the light source 120 meets Class 1 of the laser safety standard, the light may be widely emitted such that the illumination area 600 covers the entire detection area 610, as illustrated in FIG. 4C. In this case, even when the object 102 slightly moves, it is highly likely that the illumination area 600 still contains the region of the object 102 (for example, the forehead) that is expected to detect. Thus, the measurement is easily continued. In addition, the influence of deviation of the forehead position due to individual difference can be reduced.

However, if the power of light from the light source 120 exceeds Class 1 of the laser safety standard, the illumination area 600 may be set so as not to include the eyes, as illustrated in FIGS. 4A and 4B. In this case, the specific part is the eyes, and the specific part extraction area 620 is set outside the illumination area 600. In this case, the lower end of the illumination area 600 by the light source 120 is included in the detection area 610 by the image sensor 130.

3. Application Example to Head Mounted Display Apparatus

An example in which the biological measuring device 100 according to the present embodiment is mounted in a head mounted display apparatus 400 is described below.

Figure 5A:
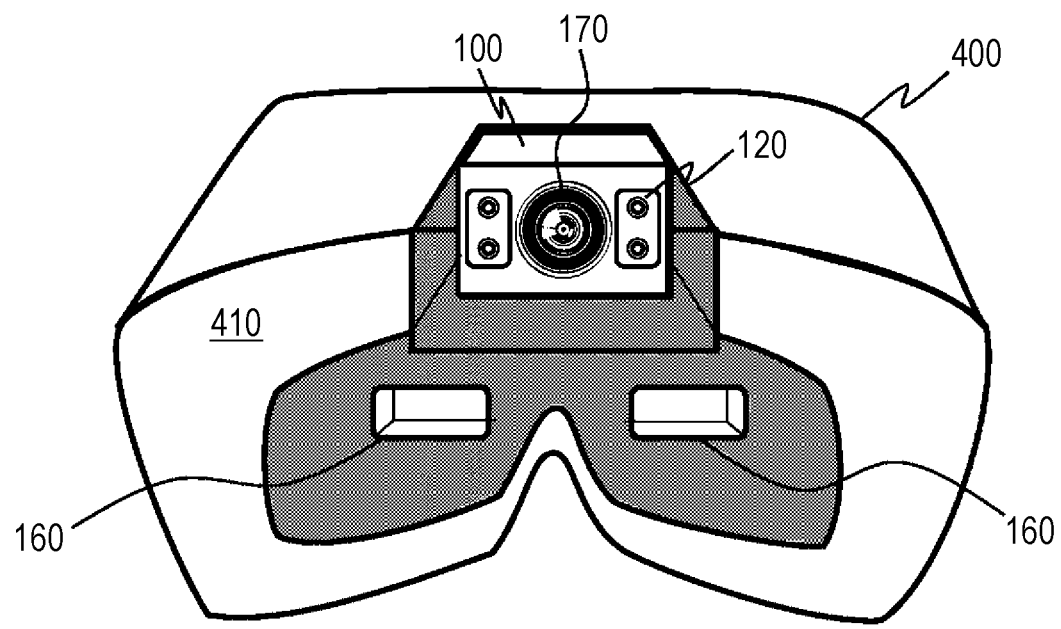
FIG. 5A is a diagram illustrating an example in which a biological measuring device is mounted on a head-mounted display device.

FIG. 5A is a diagram illustrating an example in which the biological measuring device 100 is mounted in the head mounted display apparatus 400. The head mounted display apparatus 400 includes a biological measuring device 100 and two displays 160 each connected to the biological measuring device 100. The biological measuring device 100 is disposed in the upper portion of the head mounted display apparatus 400. The two displays 160, one for the left eye and the other for the right eye, are arranged under the biological measuring device 100. The biological measuring device 100 is disposed at a distance from a contact surface 410 of the head mounted display apparatus 400 in contact with the object 102. That is, the light source 120 and a lens 170 in the biological measuring device 100 are disposed behind the contact surface 410. Note that the number of displays 160 is not limited to two, and at least one display is required.

If the distance between the object 102 and the biological measuring device 100 is small, the diffusion angle of light emitted from the light source 120 and the angle of view of the lens 170 need to be extremely increased. In contrast, according to the present embodiment, since the distance between each of the light source 120 and the lens 170 and the object 102 is relatively large, the illumination area 600 and the detection area 610 can be expanded. As a result, the design burden of a lighting system and an optical system of the biological measuring device 100 can be relieved.

For example, a task for the biometric measurement is displayed on the display 160. This task is, for example, a simple calculation or puzzle, which can be used to diagnose the brain activity of the object. When the object wears the head mounted display apparatus 400, the task is displayed on the display 160. Thus, information about the outside world can be blocked, and the object can concentrate on the task.

Figure 5B:
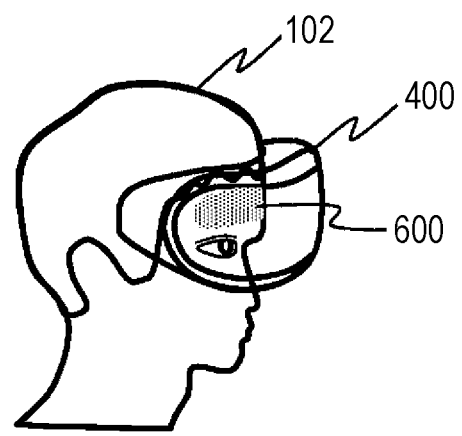
FIG. 5B is a diagram illustrating measurement of the blood flow of an object by using a head-mounted display apparatus having a biological measuring device mounted thereon.

FIG. 5B is a diagram illustrating measurement of the object 102 using the head mounted display apparatus 400 having the biological measuring device 100 mounted thereon. Since measurement is performed for the object 102 wearing the head mounted display apparatus 400, the influence of body movement of the object 102 can be reduced in the measurement. In addition, since a measurement method using a camera is employed, measurement data having spatially continuous measurement points and high resolution can be obtained.

As described above, according to the present embodiment, if a specific part of the object 102 is not located within a predetermined coordinate range in the image output from the image sensor 130 of the imaging device 110, the control circuit 140 instructs the light source 120 not to emit light. However, if the specific part is located within the coordinate range, the control circuit 140 instructs the light source 120 to emit light. In addition, if the specific part is not located within the above-described coordinate range when the control circuit 140 receives a light emission instruction from a user, the control circuit 140 suspends light emission from the light source 120. However, if the specific part is located within the above-described coordinate range, the control circuit 140 instructs the light source 120 to start light emission. If, in biometric measurement performed by emitting light from the light source 120, the specific part moves out of the coordinate range, the control circuit 140 reduces the power of light emitted from the light source 120 or stops the light emission. In addition, if the specific part is not located within the above-described coordinate range, the control circuit 140 outputs a signal indicating that the specific part is not located within the coordinate range. The signal may be sent to, for example, the display 160, and a warning message may be displayed for the user.

According to the above-described configuration, the power consumed by the light source 120 can be reduced when the positional relationship between the biological measuring device 100 and the object 102 is not appropriate.

In addition, a warning message can be sent to the user, and the user can adjust the position of the biological measuring device 100.

Embodiment 2

Embodiment 2 of the present disclosure includes a step in which the biological measuring device 100 determines whether light emission to the forehead position is appropriately performed in addition to performing the operation of Embodiment 1. In the following description, detailed description of the same operations as in Embodiment 1 is not repeated.

Figure 6:
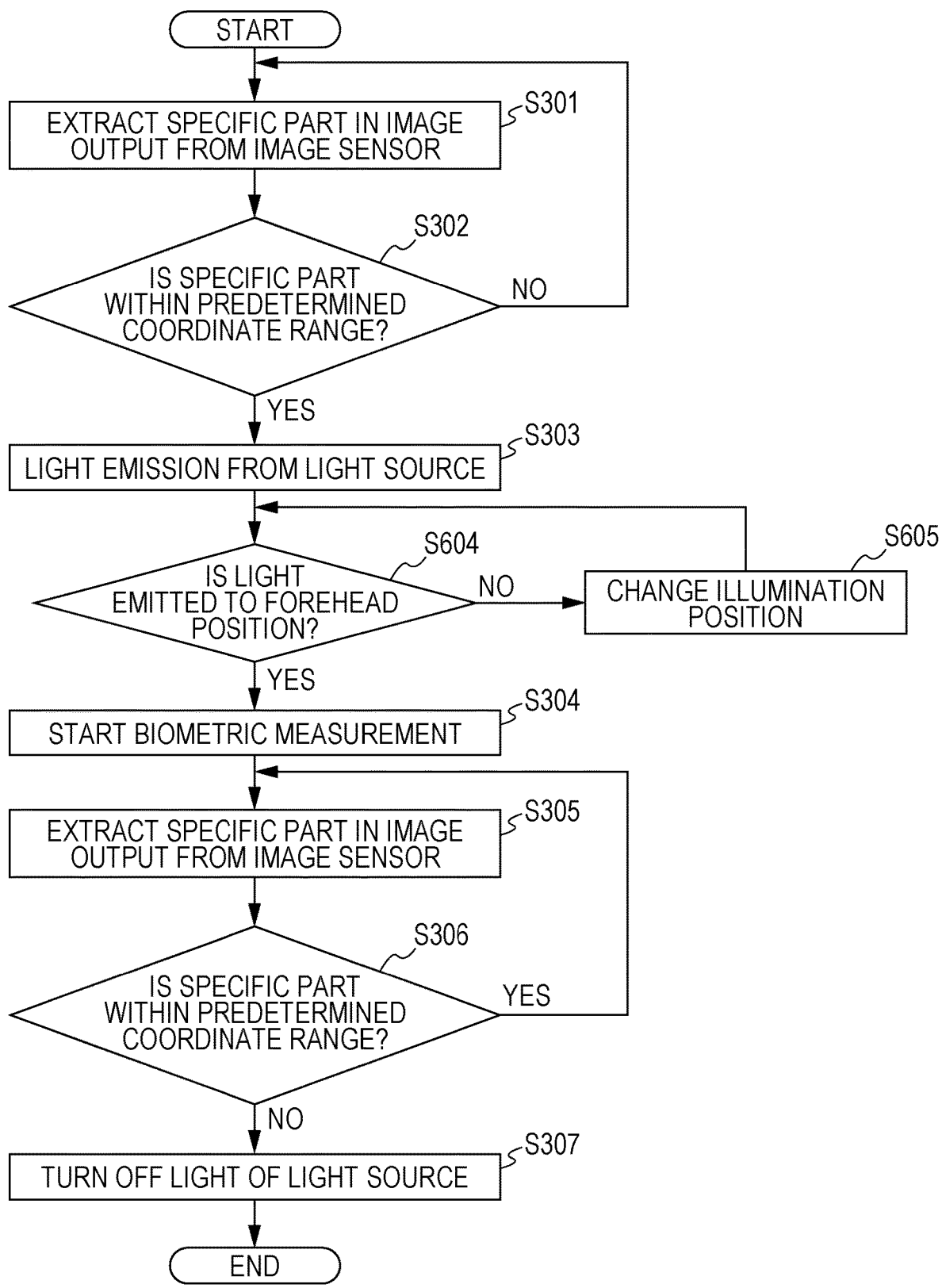
FIG. 6 is a flowchart illustrating operation performed by a biological measuring device according to Embodiment 2.

FIG. 6 is a flowchart illustrating the operation performed by the biological measuring device 100 according to Embodiment 2. In FIG. 6, the operations in steps S301 to S307 are the same as the operations illustrated in FIG. 3. According to the present embodiment, unlike the operations illustrated in FIG. 3, steps S604 and S605 are inserted between steps S303 and S304.

The biological measuring device 100 determines whether the light is correctly emitted to the forehead position after the light is emitted from the light source 120 in step S303 (step S604). In this step, the image processing circuit 150 recognizes the illumination area 600 by the light source 120 in the image output from the image sensor 130 and determines whether the illumination area 600 covers the forehead of the object 102.

Figure 7A:
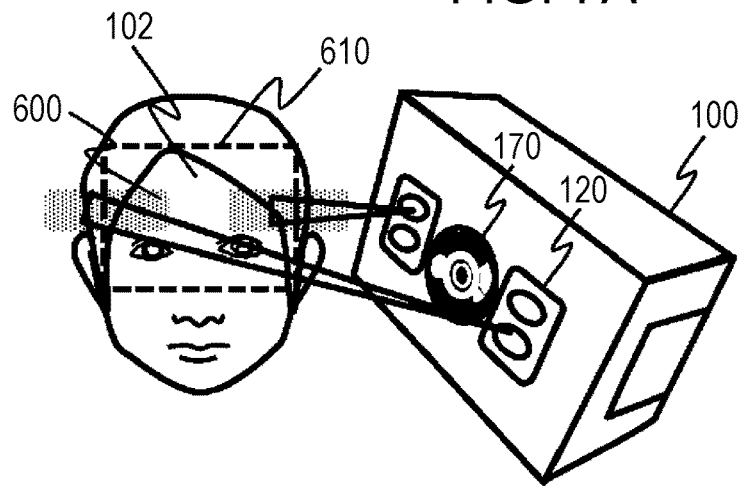
FIG. 7A is a first diagram illustrating a position of the illumination area by the light source that varies in accordance with a distance from the object.
Figure 7B:
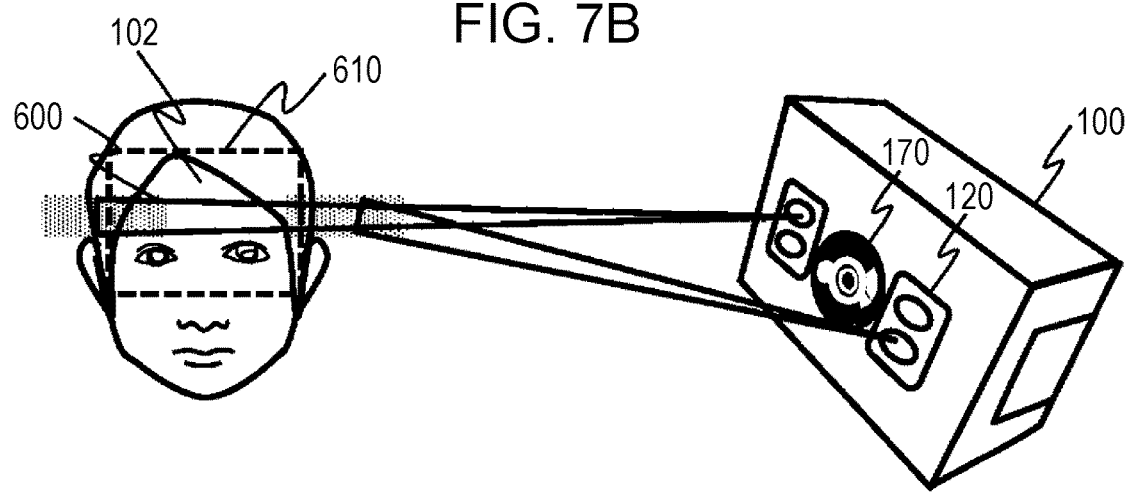
FIG. 7B is a second diagram illustrating the position of the illumination area by the light source that varies in accordance with the distance from the object.
Figure 7C:
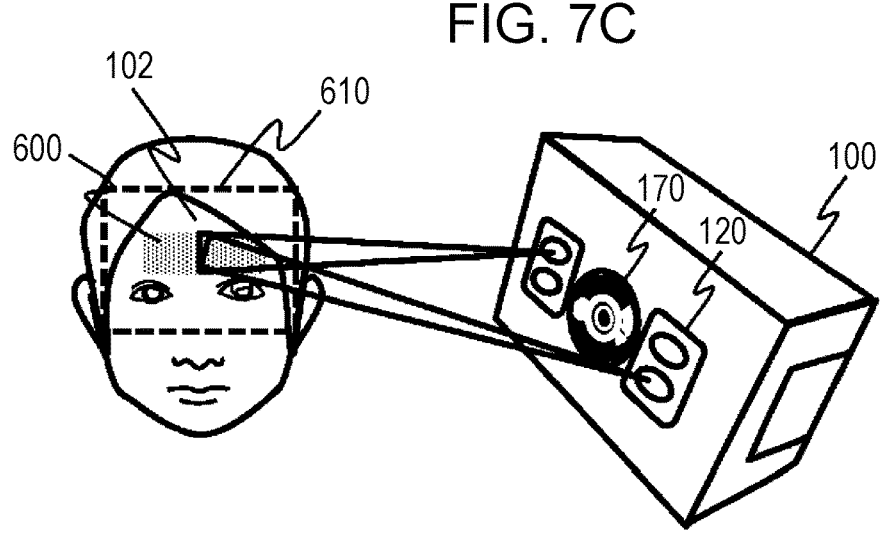
FIG. 7C is a third diagram illustrating the position of the illumination area by the light source that varies in accordance with the distance from the object.

As illustrated in FIGS. 7A to 7C, the position of the illumination area 600 by the light source 120 varies in accordance with the distance from the object 102. FIG. 7A illustrates the illumination area 600 that runs over the detection area 610 to the outside due to the biological measuring device 100 located excessively close to the object 102. This phenomenon occurs due to the parallax between the light source 120 and the lens 170. FIG. 7B illustrates deviation between the illumination area 600 and the detection area 610 that similarly occurs due to the biological measuring device 100 located excessively far from the object 102. In the cases illustrated in FIGS. 7A and 7B, the light emission direction of the light source 120 is adjusted.

Therefore, according to the present embodiment, if it is determined that the illumination area 600 does not cover the forehead, the control circuit 140 changes the illumination position of the light source 120 (step S605). For example, the control circuit 140 changes the illumination position by adjusting the angle or position of the light source 120. In this case, the biological measuring device 100 may include an actuator or a motor that is a mechanism for adjusting the angle or position of the light source 120. The mechanism may be a mechanism that enables the distance between the biological measuring device 100 and the object 102 to be variable. The biological measuring device 100 can be driven in, for example, a time of flight (TOF) mode that generates pulsed light. The control circuit 140 may measure the distance to the object 102 by using the round trip time of the pulsed light and identify the illumination direction of the light source 120 or the distance between the biological measuring device 100 and the object 102 on the basis of the principle of triangulation.

The processing in step S605 may be performed manually instead of being performed automatically by the apparatus. For example, the control circuit 140 may output a voice message or an image message "the measurement position has deviated" via a display or a loudspeaker. In response to the message, the user manually adjusts the orientation or position of the light source 120. In this case, the light source 120 may include a rotation mechanism so that the light source 120 can be manually adjusted. In addition to adjusting the light emission direction of the light source 120, the position of the illumination area 600 may be adjusted by adjusting the distance between the biological measuring device 100 and the object 102, as illustrated in FIG. 7C.

Figure 8:
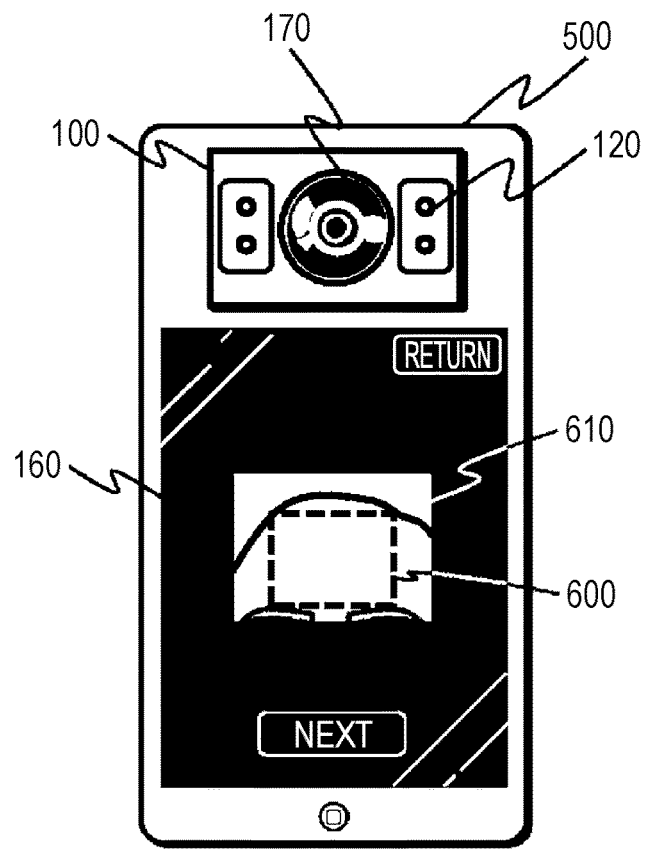
FIG. 8 is a diagram illustrating an example of a mobile terminal having a biological measuring device mounted thereon.

Such a configuration is suitable particularly for the biological measuring device 100 mounted in a mobile terminal 500, as illustrated in FIG. 8. Unlike the head mounted display apparatus 400, the mobile terminal 500 performs measurement on the object 102 that is completely away from the mobile terminal 500. Accordingly, the distance between the object 102 and the biological measuring device 100 is likely to shift. Therefore, it is effective to determine whether the position of the forehead that is the object to be measured is properly within the illumination area 600 and to output a message prompting the user to adjust the position of the mobile terminal 500 if the position is not within the illumination range 600.

As illustrated in FIG. 8, the mobile terminal 500 has the biological measuring device 100 attached thereto. The illumination area 600 and the detection area 610 are displayed on the display 160 of the mobile terminal 500 before the measurement starts. Thus, the user can determine whether the part (for example, the forehead) of the object 102 to be measured is located at an appropriate position and can be measured correctly. When the biometric measurement is started, a task is displayed on the display 160. Accordingly, the display 160 of the mobile terminal 500 can be used for both checking the measurement environment and displaying the task.

As described above, according to the present embodiment, the image processing circuit 150 of the biological measuring device determines whether the target portion of the object 102 is located in the illumination area 600. The control circuit 140 outputs a warning signal if the target portion of the object 102 is not located within the illumination area 600. The image processing circuit 150 calculates the coordinates of the forehead in the image and determines whether the calculated coordinates of the forehead are within the illumination area 600. If the coordinates of the forehead are not within the illumination area 600, the control circuit 140 outputs a warning signal. For example, the control circuit 140 instructs the display 160 to display an image indicating that at least one selected from a group consisting of the position of the light source 120, the orientation of the light source 120, the position of the biological measuring device 100, and the orientation of the biological measuring device 100 is to be changed.

Figure 9:
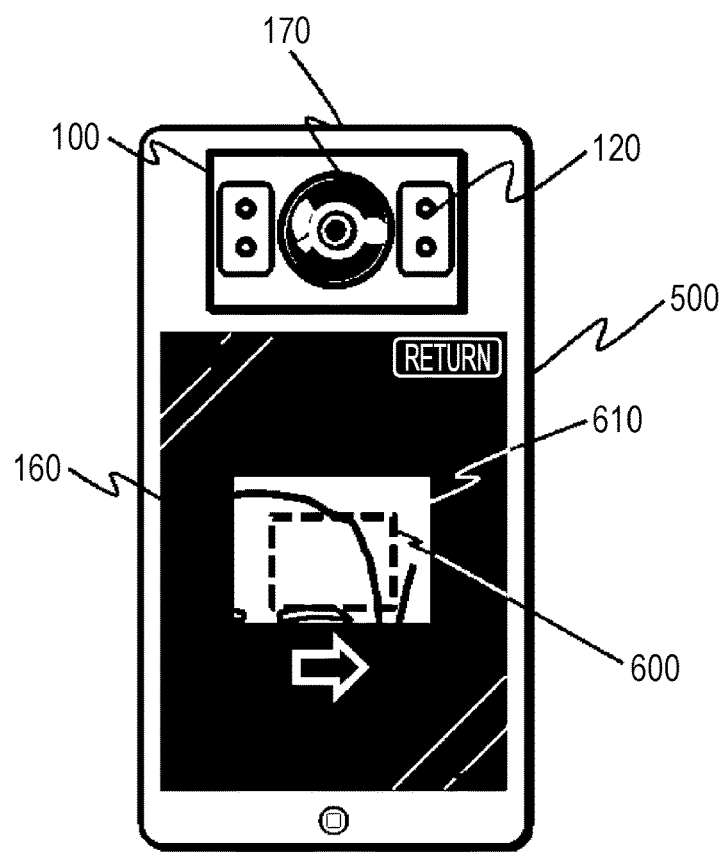
FIG. 9 is a diagram illustrating an example in which an arrow is displayed on a display of the mobile terminal.
Figure 10:
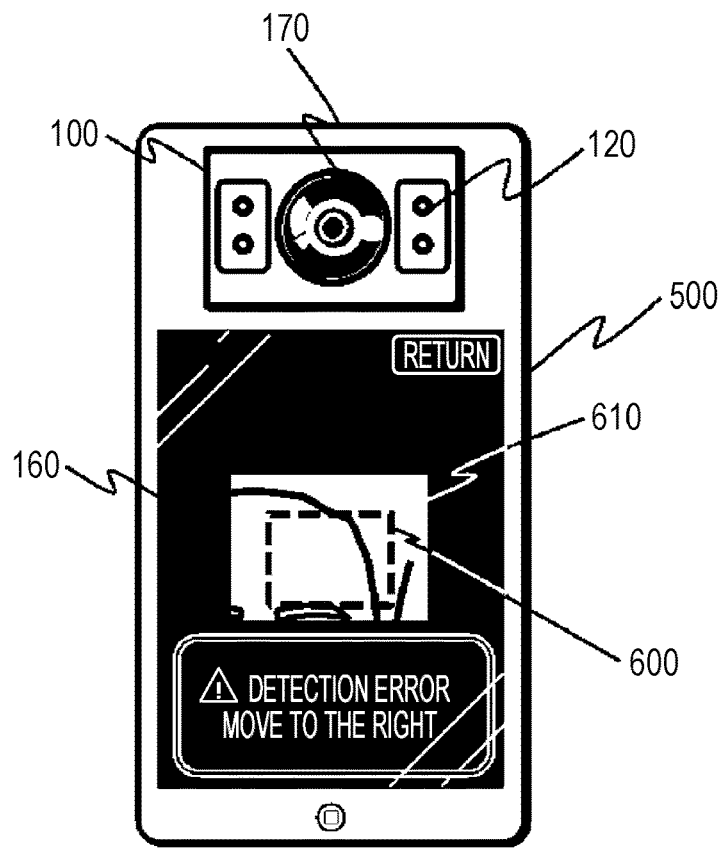
FIG. 10 is a diagram illustrating an example in which a message is displayed on the display of the mobile terminal.
Figure 11:
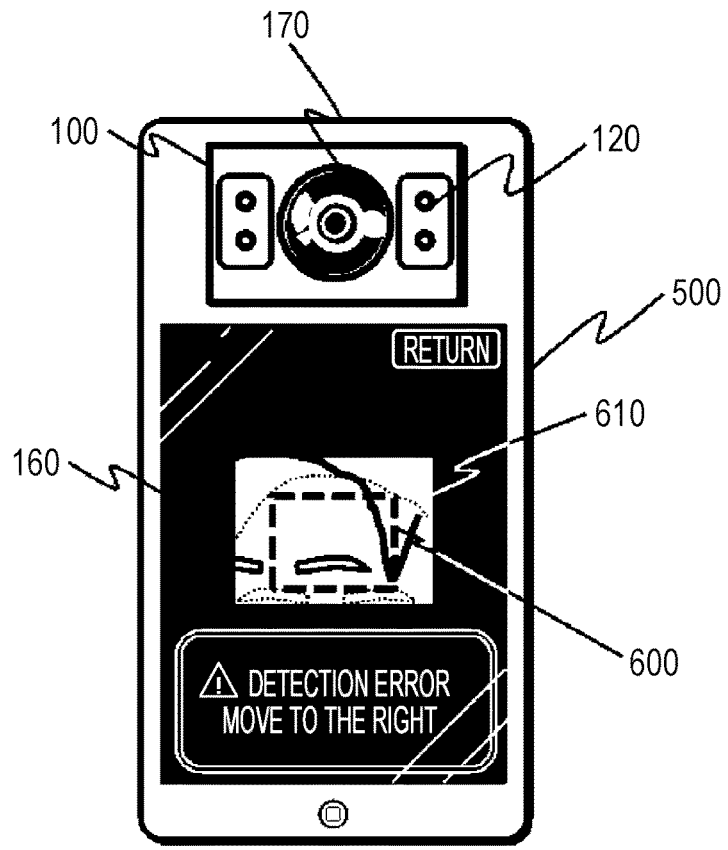
FIG. 11 is a diagram illustrating an example in which the position at which the outline of the face is to be placed is indicated on the display of the mobile terminal.

FIGS. 9 to 11 illustrate examples of the mobile terminal 500 including the display 160 having such images displayed thereon. In the example illustrated in FIG. 9, an arrow is displayed on the display 160. This arrow prompts the user to move the position of the forehead to the right with respect to the light source 120 or the biological measuring device 100 because the coordinate of forehead has deviated to the left with respect to the illumination area 600.

In addition, in the example illustrated in FIG. 10, a message is displayed on the display 160. This message prompts the user to move the position of the forehead to the right with respect to the light source 120 or the biological measuring device 100 because the coordinate of the forehead has deviated to the left with respect to the illumination area 600.

In the example illustrated in FIG. 11, the display 160 displays a message and a dotted line indicating the position at which the contour of the face is to be placed. This displayed image prompts the user to move the forehead to the right with respect to the light source 120 or the biological measuring device 100 because the coordinate of the forehead has deviated to the left with respect to the illumination area 600.

By using such a configuration, biometric measurement is performed only when the target portion, such as the forehead, is appropriately positioned within the illumination area. As a result, the power consumed by the light source 120 can be reduced.

According to the present embodiment, determination of the position of the target portion may be periodically performed during the biometric measurement in addition to when the measurement is started. For example, if the position of the forehead moves outside the illumination range during measurement, light emission from the light source 120 may be stopped, or the power of light emission may be reduced. By applying such control, power consumption during measurement can be reduced.

Figure 12:
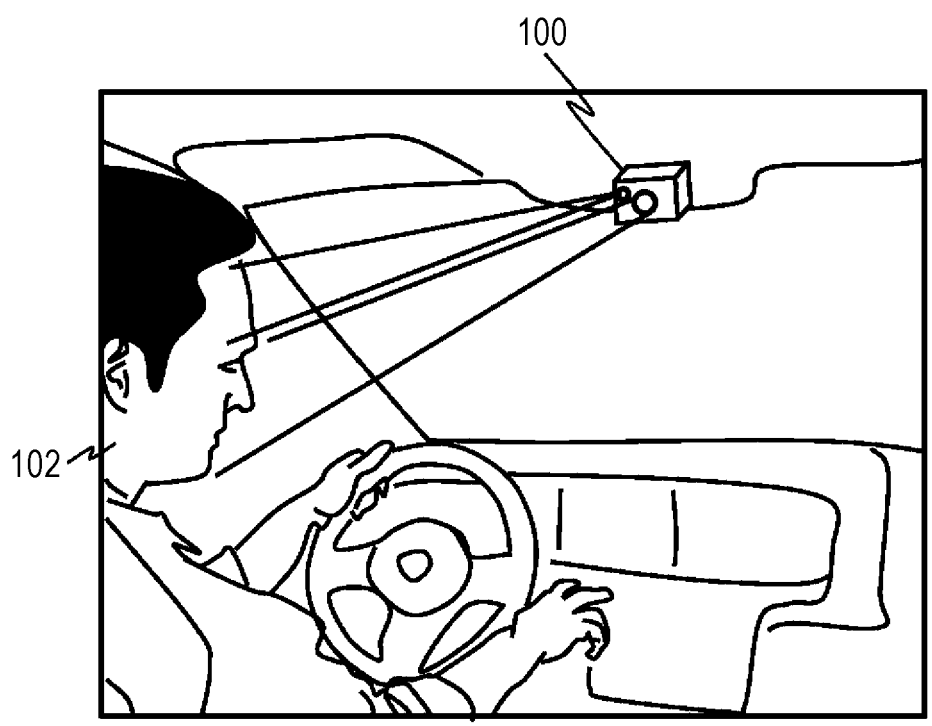
FIG. 12 is a diagram illustrating an example of a biological measuring device mounted in a vehicle.

While the above embodiments have been described with reference to the example in which the biological measuring device 100 is mounted in the head mounted display apparatus 400, the mobile terminal 500, or the like, the present disclosure is not limited thereto. For example, as illustrated in FIG. 12, the biological measuring device 100 may be mounted in a vehicle. In the example illustrated in FIG. 12, the biological measuring device 100 is attached to, for example, an upper section of a windshield so that the driver in the vehicle can be measured.

According to the above-described embodiments, a single image sensor 130 performs capture of the image of the object 102 and measurement of biological information. However, a configuration in which these functions are performed by two devices may be employed. That is, the imaging device 110 (FIG. 1A) in the biological measuring device 100 may include a photodetector in addition to the image sensor that captures the image of the object 102. The photodetector detects light emitted from the light source 120 and reflected or scattered by the object 102. In this case, the photodetector need not include a plurality of light receiving elements arranged two-dimensionally. The photodetector may include a plurality of light receiving elements arranged one-dimensionally or a single light receiving element in accordance with an application.

What is claimed is:

1. A biological measuring device comprising:
    a light source that emits first light illuminating an area on a living body;
    an imaging device that detects second light returned from the living body and acquires a first image including at least part of the living body; and
    a control circuit that controls the light source, wherein
    if a specific part of the living body is not located in a predetermined coordinate range in the first image, the control circuit restricts emission of the first light from the light source, and
    the predetermined coordinate range is set outside the area.

2. The biological measuring device according to claim 1, further comprising:
    an image processing circuit, wherein
    the image processing circuit determines whether the specific part of the living body is located in the predetermined coordinate range in the first image.

3. The biological measuring device according to claim 1, wherein
    if the specific part of the living body is not located in the predetermined coordinate range in the first image, the control circuit causes the light source not to emit the first light, and if the specific part is located in the predetermined coordinate range in the first image, the control circuit causes the light source to emit the first light and acquires biological information about the living body based on the second light detected by the imaging device.

4. The biological measuring device according to claim 3, wherein
if the specific part moves from inside to outside of the predetermined coordinate range in the first image during acquisition of the biological information, the control circuit causes the light source to reduce power of the first light or causes the light source to stop emission of the first light.

5. The biological measuring device according to claim 1, wherein
if the specific part is not located in the predetermined coordinate range in the first image, the control circuit further outputs a signal indicating that the specific part is not located in the predetermined coordinate range in the first image.

6. The biological measuring device according to claim 1, further comprising:
a display, wherein
the control circuit causes the display to display the first image.

7. The biological measuring device according to claim 6, wherein
if the specific part is not located in the predetermined coordinate range in the first image, the control circuit causes the display to display a second image indicating that at least one selected from the group consisting of a position of the light source, a position of the biological measuring device, an orientation of the light source, and an orientation of the biological measuring device is to be changed.

8. The biological measuring device according to claim 1, wherein
the area on the living body is included in the at least part of the living body.

9. The biological measuring device according to claim 1, wherein
the specific part is at least one selected from the group consisting of eyes, a nose, a mouth, ears, and eyebrows.

10. The biological measuring device according to claim 2, wherein
the image processing circuit further determines whether a target portion of the living body is located in the area in the first image, and
if the target portion is not located in the area in the first image, the control circuit outputs a signal for warning.

11. The biological measuring device according to claim 10, wherein
the target portion is a forehead,
the image processing circuit calculates coordinates of the forehead in the first image and determines whether the coordinates of the forehead are in the area, and
the control circuit outputs the signal for warning if the coordinates of the forehead are not in the area.

12. The biological measuring device according to claim 11, further comprising:
a display, wherein
if the coordinates of the forehead are not in the area, the control circuit causes the display to display a third image indicating that at least one selected from the group consisting of a position of the light source, a position of the biological measuring device, an orientation of the light source, and an orientation of the biological measuring device is to be changed.

13. A biological measuring device comprising:
a light source that emits first light illuminating an area on a living body;
an imaging device that detects second light returned from the living body and acquires a first image including at least part of the living body; and
a control circuit that controls the light source, wherein
if a position of eyes of the living body overlaps the area in the first image, the control circuit restricts emission of the first light from the light source.

14. A head mounted display apparatus wearable on a head of a living body, the head mounted display apparatus comprising:
the biological measuring device according to claim 1; and
a display connected to the biological measuring device.

* * * * *